(12) United States Patent
Sharma

(10) Patent No.: US 7,651,871 B2
(45) Date of Patent: Jan. 26, 2010

(54) DEVICE FOR FORMING MAGNETIC WELL FOR NANOPARTICLES

(75) Inventor: Manish Sharma, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 673 days.

(21) Appl. No.: 11/290,879

(22) Filed: Nov. 30, 2005

(65) Prior Publication Data

US 2007/0122898 A1   May 31, 2007

(51) Int. Cl.
*G01N 33/553* (2006.01)
*C12M 1/34* (2006.01)

(52) U.S. Cl. .................. 436/526; 422/58; 435/287.2; 977/962

(58) Field of Classification Search .............. 422/50, 422/55, 58; 435/287.1, 287.2, 283.1; 977/902, 977/904, 920, 921, 922, 962; 436/526
See application file for complete search history.

(56) References Cited

U.S. PATENT DOCUMENTS 5,466,574 A * 11/1995 Liberti et al. ............... 435/5

OTHER PUBLICATIONS

G. Li et al., Detection of Single Micron-Sized Magnetic Bead and Magnetic Nanoparticles Using Spin-Valve Sensors for Biological Applications, 93 J. Appl. Phys. 7557-7559 (2003).*
H. Lee et al., Manipulation of Biological Cells Using a Microelectromagnet Matrix, 85 Appl. Phys. Lett. 1063-1065 (2004).*
L. Lagae et al., On-Chip Manipulation and Magnetization Assessment of Magnetic Bead Assemblies by Integrated Spin-Valve Sensors, 91 J. Appl. Phys. 7445-7447 (2002).*
Definition of "oscillate" available at http://www.merriam-webster.com/dictionary/oscillate, Merriam-Webster Online Dictionary (2009).*
Graham et al., "Magnetoresistive-based biosensors and biochips," Trends in Biotechnology, vol. 22, No. 9, pp. 455-462 (Sep. 2004).

* cited by examiner

*Primary Examiner*—Glenn Caldarola
*Assistant Examiner*—Randy Boyer

(57) ABSTRACT

A device includes a plurality of structures, each structure including at least one ferromagnetic layer having fringe fields. Fringe fields of the structures interact to form a magnetic well for nanoparticles. This device may be adapted for biosensing, wherein the magnetic well is formed about a probe area.

27 Claims, 10 Drawing Sheets

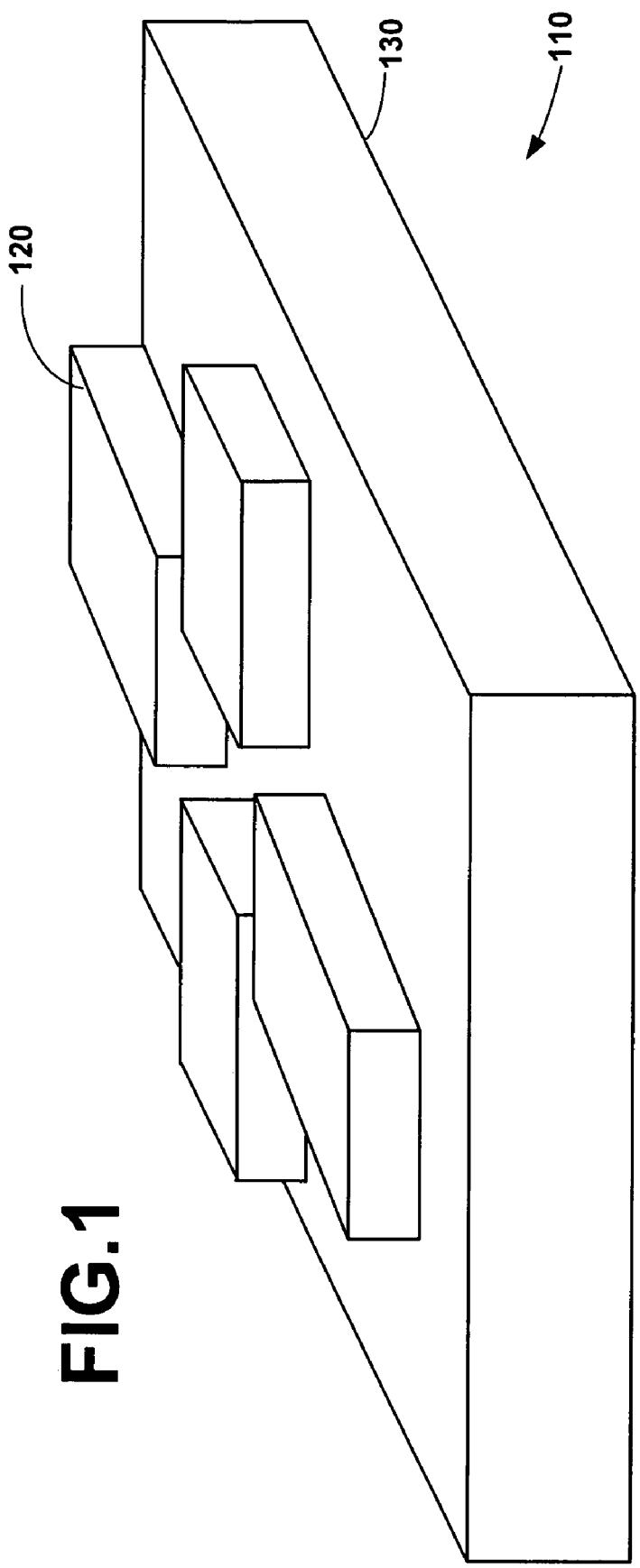

FIG. 9
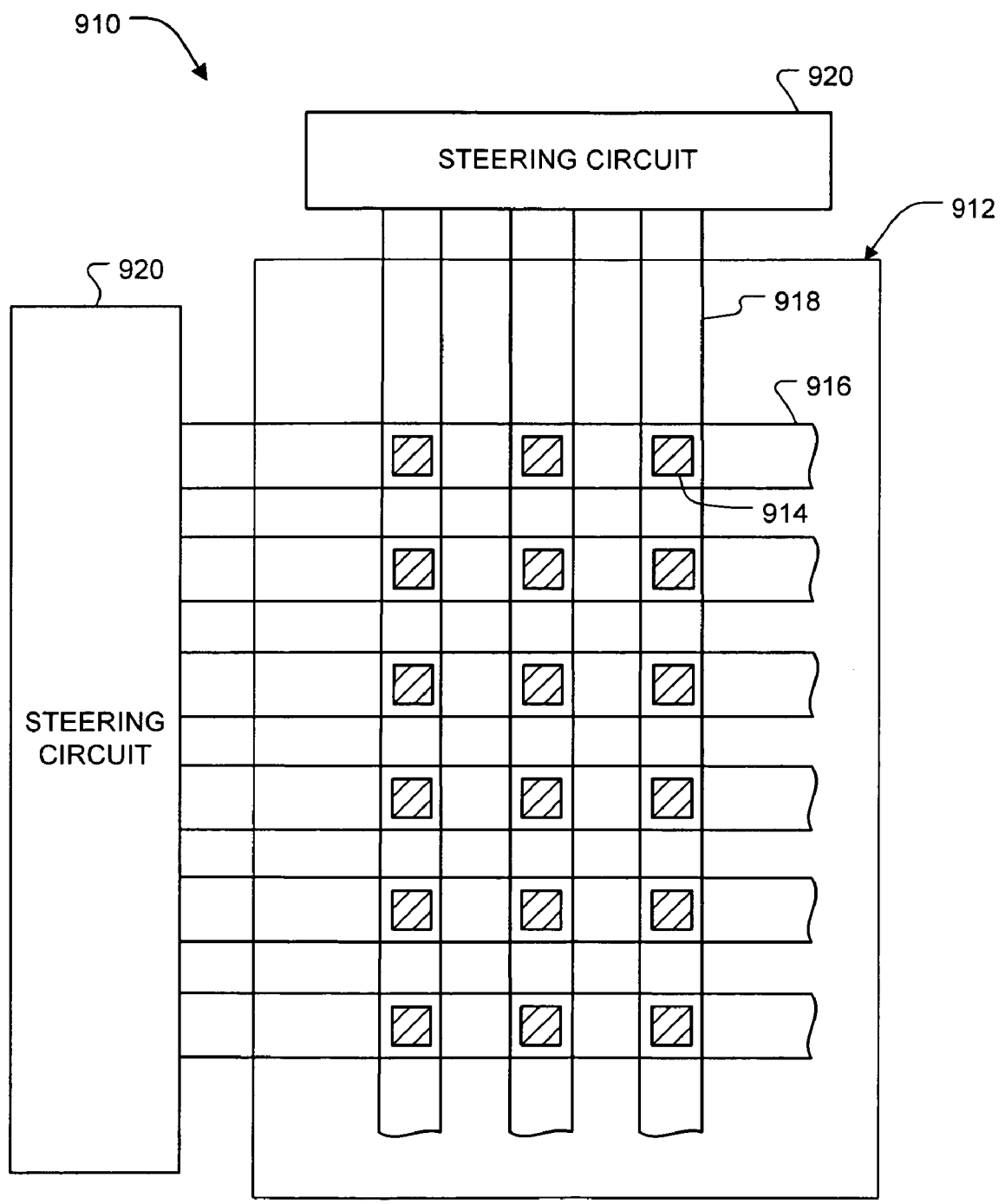
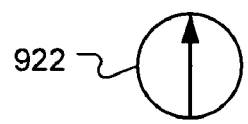

DEVICE FOR FORMING MAGNETIC WELL FOR NANOPARTICLES

BACKGROUND

Certain biosensing systems use magnetoresistive (MR) sensors to detect biologically functionalized nanometer-sized magnetic labels. For instance, a biomolecule under test is immobilized on magnetic labels and passed over an array of probe molecules. An MR sensor is used to detect the presence of the magnetic labels. Magnetic labels not bound to the probe molecules are then washed away, and the MR sensor is once again used, this time to detect the presence of magnetic labels that are bound to the probe molecules. Resistance of the MR sensor is proportional to the net magnetic moment of the magnetic labels. A significant change in resistance after washing away the unbound magnetic labels indicates that the magnetic labels did not bind to the probe molecules.

Although these biosensing systems test for the presence of certain biomolecules, they do not test the mechanical properties of biomolecules. Yet in biological testing, there is value in being able to move and manipulate magnetic labels. Valuable information can be learned by testing the mechanical properties of a magnetic label that has bonded to a probe, whether that of a protein detected with an antibody or a DNA fragment hybridizing with another DNA fragment.

SUMMARY

According to one aspect of the present invention, a device includes a plurality of structures, each structure including at least one ferromagnetic layer having fringe fields. Fringe fields of the structures interact to form a magnetic well.

According to another aspect of the present invention, the device is adapted for biosensing. The magnetic well is formed about a functionalized area. The biosensing device can move and manipulate magnetic labels.

Other aspects and advantages of the present invention will become apparent from the following detailed description, taken in conjunction with the accompanying drawings, illustrating by way of example the principles of the present invention.

BRIEF DESCRIPTION OF THE DRAWINGS

FIG. 1 is an illustration of a device in accordance with an embodiment of the present invention.

FIG. 9 is an illustration of a biosensor chip in accordance with an embodiment of the present invention.

DETAILED DESCRIPTION

Referring to FIG. 1, a device 110 includes a plurality of structures 120 on a substrate 130. Each structure 120 includes at least one layer of ferromagnetic material having its magnetic domains aligned in the same direction along an easy axis. The net magnetic moment of each structure 120 can be oriented between two stable orientations. In one stable orientation, the net magnetic moment is aligned in one direction along the easy axis. In the other stable orientation, the net magnetic moment is aligned in the opposite direction along the easy axis.

As shown in FIGS. 2a-2e, each structure 120 has fringe fields (F) emanating at its ends. Ends of the structures 120 are placed close enough together such that their fringe fields interact to form a magnetic field that can trap nanoparticles made of ferromagnetic or paramagnetic material (the nanoparticles are represented as dots in FIG. 2a). This magnetic field will hereinafter be referred to as a "magnetic well."

Size of the nanoparticles may be less than 100 nm. Exemplary paramagnetic nanoparticle materials include, without limitation, nickel oxides and iron oxides such as $Fe_2O_3$, $Fe_3O_4$, Ni, NiFe, CoFe, Co, Fe, and NiFeCo. Ferromagnetic materials include NiFe, NiFeCo and CoFe, alloys of Ni, Fe and Co, certain oxides of Ni, Fe and Co, and ferromagnetic materials doped with amorphising agents such as C, N, Cr, Nb and B. If particles made with ferromagnetic materials are "small enough", they become paramagnetic. The particles are "small enough" when their volume V satisfies $K*V<k_b*T$, where K is the anisotropy constant of the material, V is volume of the particle, $k_b$ is the Boltzmann constant, T is the temperature. An exemplary size of a "small enough" particle is about 25 nm.

Paramagnetic nanoparticles have a small and positive susceptibility to the magnetic well. They are slightly attracted by the magnetic well, but do not retain their magnetic properties when removed from the magnetic well. Ferromagnetic nanoparticles have a large and positive susceptibility to the magnetic well. They exhibit a strong attraction to the magnetic well and are able to retain their magnetic properties when removed from the magnetic well. Among the advantages of the paramagnetic particles, they don't clump together.

Figure 2A:
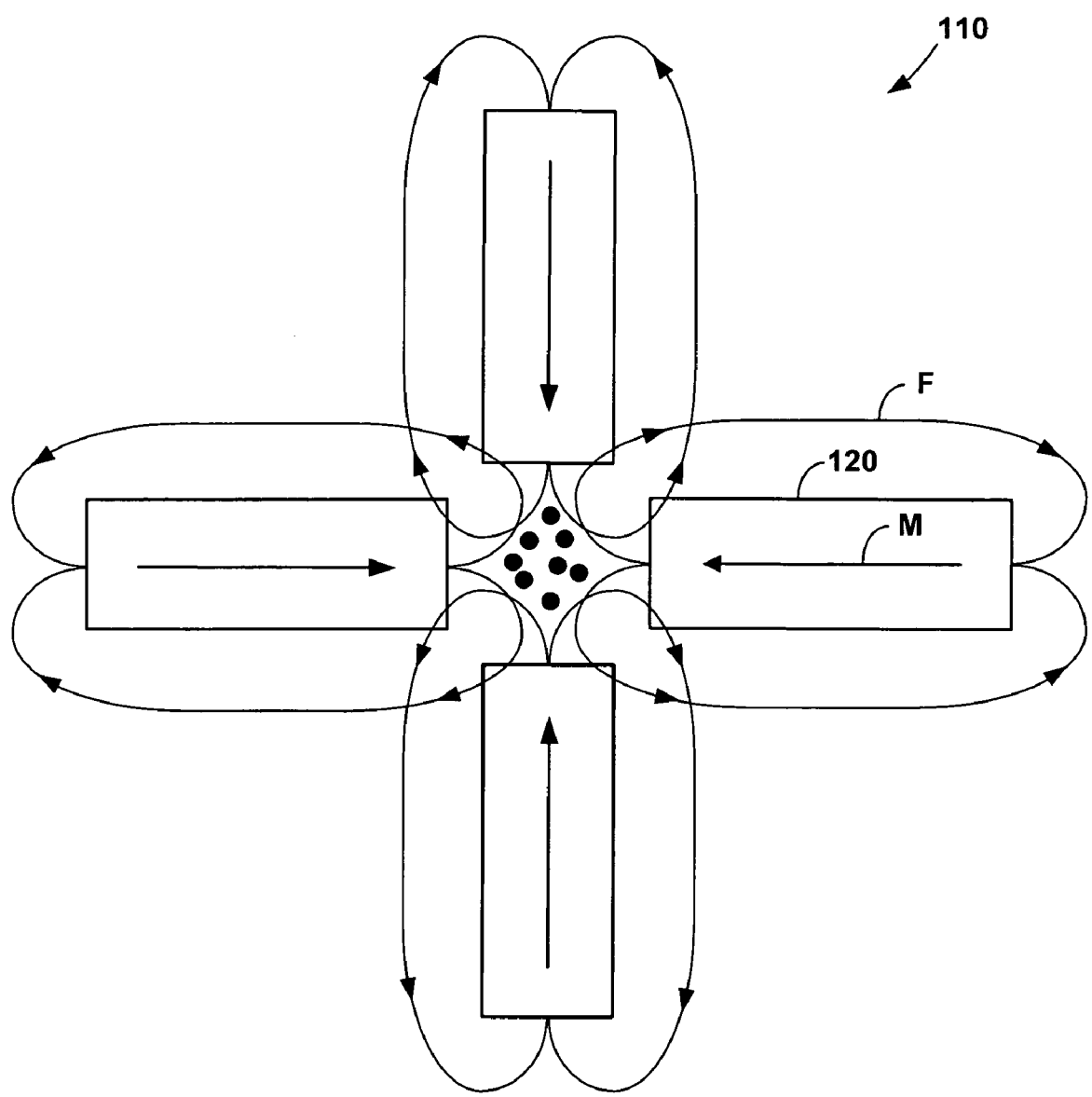
FIGS. 2a-2e show different magnetization orientations of the device of FIG. 1.

FIGS. 2a-2e show different possible magnetization orientations for the device 110. FIG. 2a shows an orientation in which all magnetization vectors point radially inward. When the device 110 has the magnetization orientation shown in FIG. 2a, the fringe field interactions produce a net magnetic moment of zero.

Figure 2B:
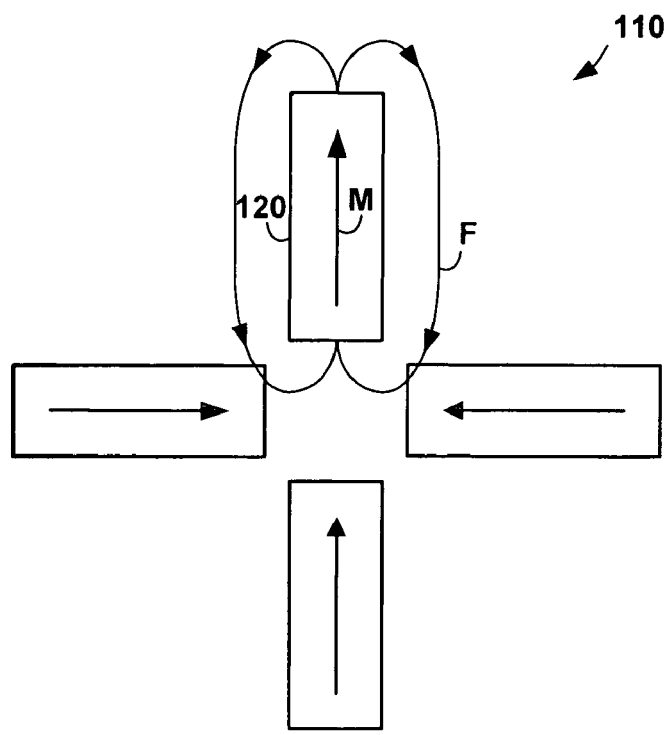
Figure 2C:
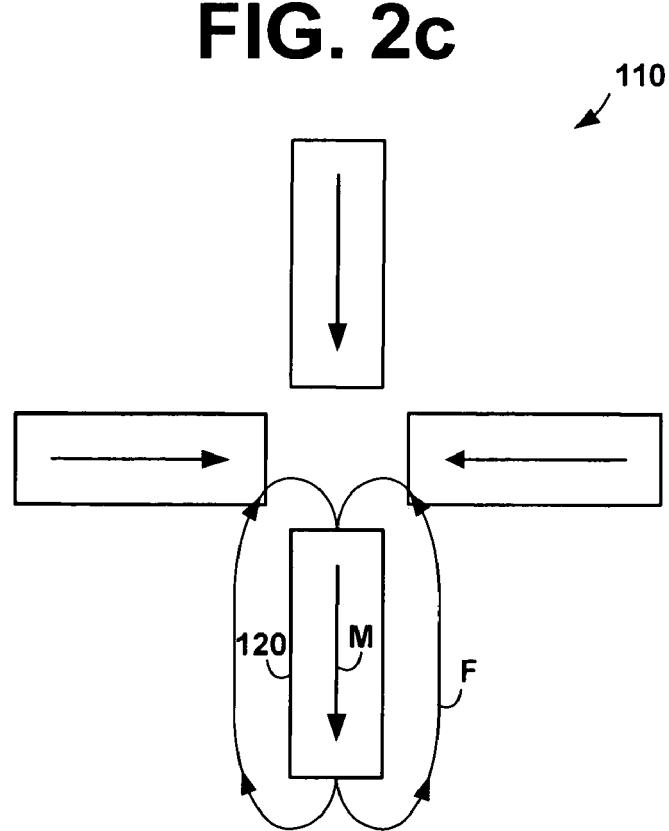
Figure 2D:
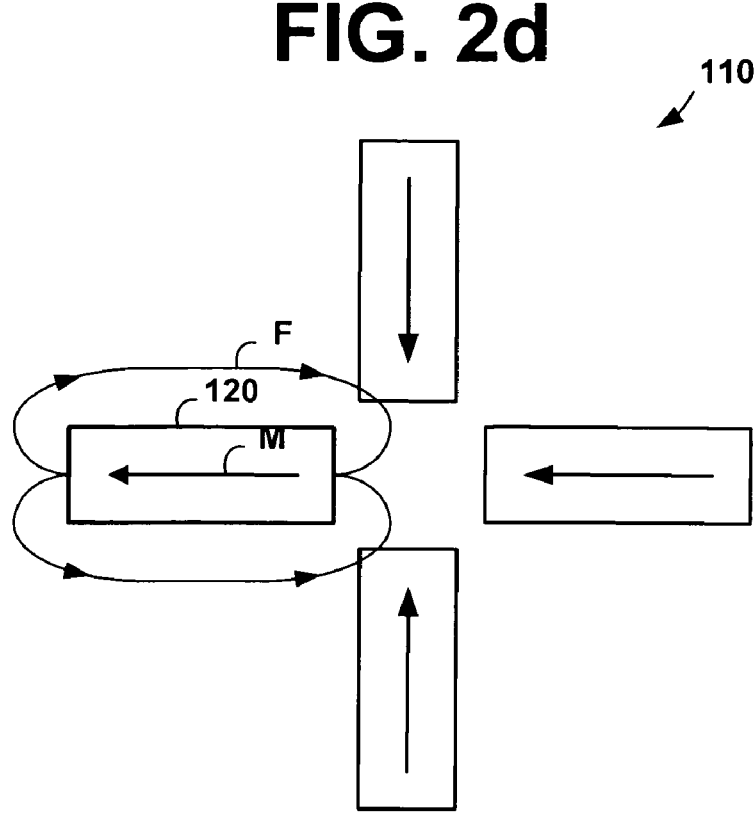
Figure 2E:
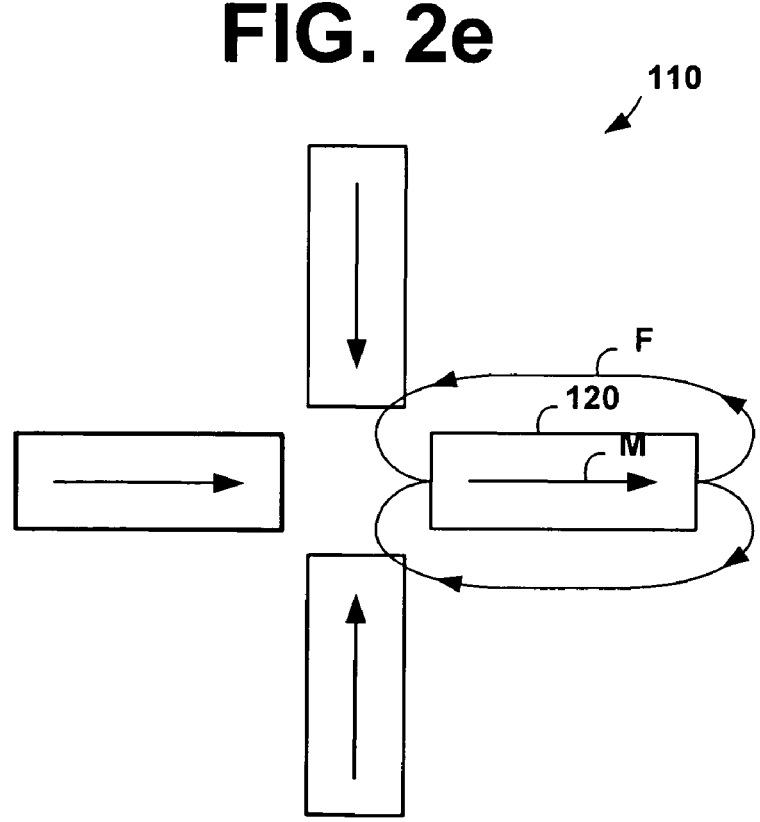

FIG. 2b shows a magnetization orientation where the magnetization of the upper structure 120 is re-oriented to the opposite direction. FIG. 2c shows a magnetization orientation where the magnetization of the lower structure 120 is re-oriented to the opposite direction. FIG. 2d shows a magnetization orientation where the magnetization of the left structure 120 is re-oriented to the opposite direction. FIG. 2e shows a magnetization orientation where the magnetization of the right structure 120 is re-oriented to the opposite direction. The different magnetization orientations give the magnetic well a non-zero magnetic moment.

The possible magnetization orientations of the device 110 are not limited to those shown in FIGS. 2a-2e. Moreover, more than one magnetization vector may be re-oriented at a time.

By selectively switching the device 110 between different magnetization orientations, the magnetic well can be made to oscillate. When the magnetic well is oscillated, oscillatory forces are applied to trapped nanoparticles. By switching the device from the orientation shown in FIG. 2a to an orientation that causes a non-zero magnetic moment, the magnetic well can apply a single, unidirectional force to trapped nanoparticles.

Let B denote the magnetic field resulting from the fringe field interaction, and let m denote the net magnetic moment of a nanoparticle (B and m are vectors). For any magnetic particle of moment m in a magnetic field B, the magnetic field applies a mechanical force (F) on the nanoparticle:

$$F = -m \cdot \text{grad}(B),$$

where grad(B) is the gradient of the vector B. A large mechanical force can be applied to ferromagnetic particles since they have a large m for a given size. In contrast, paramagnetic particles have a zero moment so they experience a force only when a gradient field (varying in space) is applied in combination with a DC biasing field (i.e., a DC field that, while applied, causes the paramagnetic nanoparticles to have a non-zero moment).

The frequency of oscillation depends largely on particle size and other forces that are present (e.g., the viscosity of a fluid containing the nanoparticles, attractions between nanoparticles, possible accumulation of charges and van der Waals and other forces being present between the nanoparticles). Typical oscillation frequencies in fluids can be expected to be anywhere from several Hz to several tens of kHz.

A device according to the present invention is not limited to any particular number of structures 120, any particular geometry for the structures 120, or any particular arrangement of the structures 120. The exemplary device 110 of FIG. 1 includes four rectangular structures that are radially arranged and angularly displaced by 90 degrees.

Figure 3:
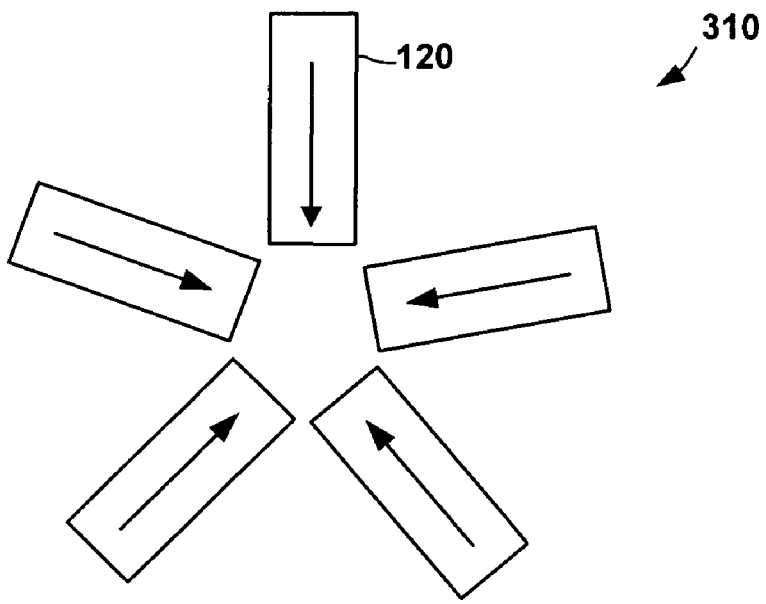
FIG. 3-4 are illustrations of devices in accordance with other embodiments of the present invention.
Figure 4:
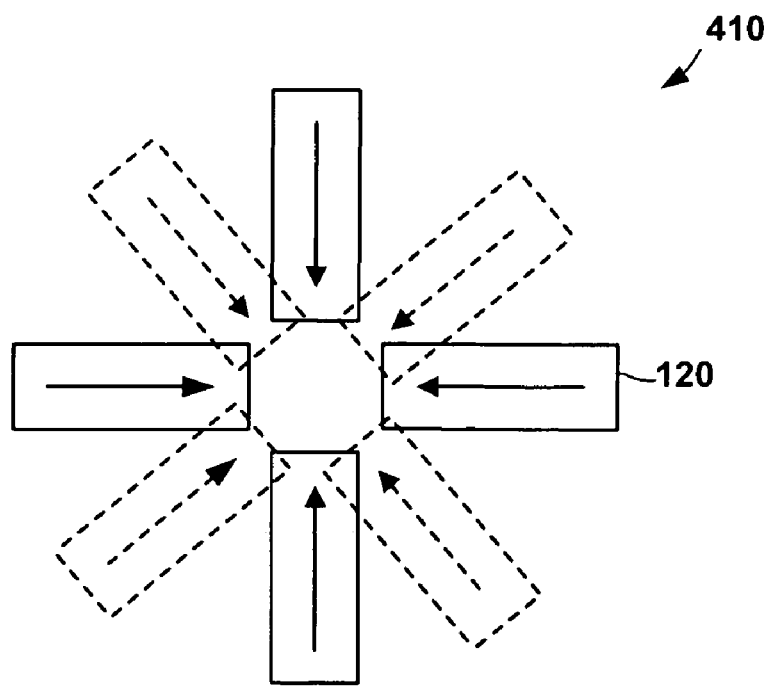

FIGS. 3 and 4 show devices 310 and 410 with different numbers and arrangements of structures 120. The exemplary device 310 of FIG. 3 includes five rectangular structures radially arranged and displaced by 72 degrees.

The exemplary device 410 of FIG. 4 includes an upper plane (shown in solid) and a lower plane (shown in dash). Each plane has four structures arranged radially. The structures of the upper plane may be aligned with the structures of the lower plane, or the upper plane may be rotated relative to the lower plane (as shown in FIG. 4). Fringe fields of all eight structures interact to form a magnetic well.

The structures 120 are not limited to any particular type of ferromagnetic layer arrangement. The different types of arrangements include, without limitation, ferromagnets, synthetic ferrimagnets and antiferromagnets. These three types of arrangements are illustrated in FIGS. 5a, 5b and 5c.

Figure 5A:
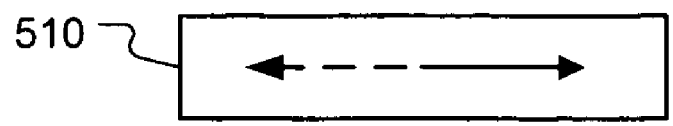
FIGS. 5a-5c are illustrations of different types of structures for a device according to the present invention.
Figure 5B:
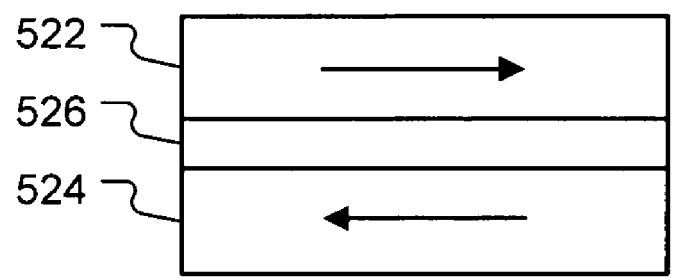
Figure 5C:
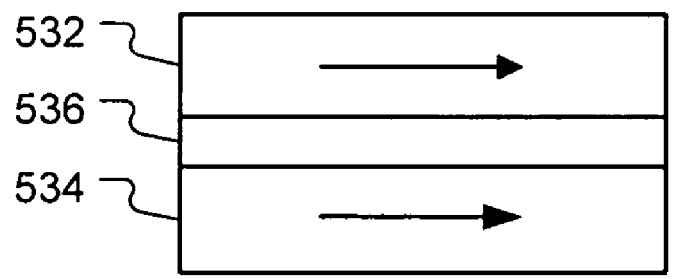

Reference is now made to FIG. 5a, which shows a ferromagnet 510 having a single layer of ferromagnetic material, such as NiFe, NiFeCo or CoFe. The ferromagnet 510 has a magnetization (represented by vector M1) that switches between two stable orientations along its easy axis. The magnetization vector shown in solid is at one stable orientation, and the magnetization vector shown in dash is at the other stable orientation.

Figure 6A:
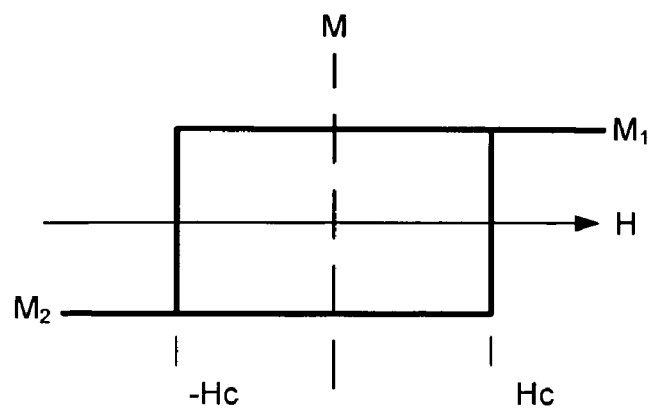
FIGS. 6a-6d are illustrations of exemplary H-M loops for a ferromagnet, a balanced synthetic ferrimagnet, an unbalanced synthetic ferrimagnet, and an antiferromagnet.

FIG. 6a shows an H-M loop for the ferromagnet 510. Coercivity is denoted by $H_c$. The magnetization vector of the ferromagnet 510 is switched to one orientation by applying an external magnetic $H > H_c$ along the easy axis. The magnetization vector of the ferromagnet 510 is switched to the other orientation by applying an external magnetic $H > H_c$ in the opposite direction along the easy axis.

Thus, the magnetization vector of each ferromagnet will have a net magnetic moment of either $M = M_1$ (in the first orientation) or $M = M_2$ (in the second orientation). If each structure 120 of the device 110 of FIG. 1 includes a single ferromagnet, the device 110 will have $2^4$ possible magnetization orientations.

The ferromagnet 510 is large relative to the nanoparticles. For example, the ferromagnet 510 may be as follows for 0.1 μm-0.2 μm nanoparticles: a single layer of NiFeCo having a thickness of 5 nm and an overall size of 0.5 μm×1.0 μm. Actual size of the ferromagnet 510 will depend on factors including, but not limited to, the ferromagnet material, and distance between the ferromagnets 510 and the region where the nanoparticles will be trapped.

Reference is now made to FIG. 5b, which illustrates a synthetic ferrimagnet 520 having first and second ferromagnetic layers 522 and 524 separated by a spacer layer 526. Each ferromagnetic layer 522 and 524 has a magnetization vector oriented along its easy axis. The spacer layer 526 may be made of an electrically conductive, magnetically non-conductive material such as Ru, Pd, Re, Rh or Cu. The material and thickness of the spacer layer 526 are selected to promote strong antiferromagnetic exchange coupling between the first and second ferromagnetic layers 522 and 524. Thus, magnetization vectors of the two ferromagnetic layers 522 and 524 always point in opposite directions.

The coercivity of each ferromagnetic layer 522 and 524 is determined by its thickness, shape, selection of material, etc. Moreover, the synthetic ferrimagnet 520 has a net magnetization that is equal to the difference between the magnetization of the first and second layers 522 and 524. Thus, the net magnetization of the synthetic ferrimagnet 520 is substantially lower than the magnetization of either ferromagnetic layer 522 or 524.

The synthetic ferrimagnet 520 may be balanced. In a balanced synthetic ferrimagnet 520, the coercivities of the two ferromagnetic layers 522 and 524 are equal, giving the synthetic ferrimagnet 520 a net coercivity of approximately zero. The balanced synthetic ferrimagnet can be switched quickly, with a low external magnetic field.

Figure 6B:
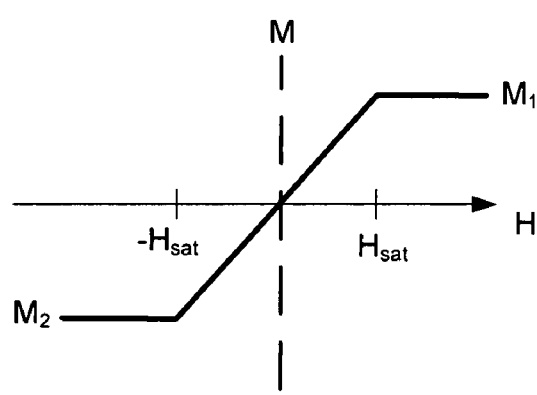

FIG. 6b shows an H-M loop for a balanced synthetic ferrimagnet 520. When an external magnetic field $H > H_{sat}$ is applied, the balanced synthetic ferrimagnet 520 switches to a first stable orientation. When an external magnetic field $H < -H_{sat}$ is applied, the balanced synthetic ferrimagnet 520 switches to a second stable orientation. For $-H_{sat} < H < H_{sat}$, the balanced synthetic ferrimagnet 520 has a net magnetic moment (M) that varies between $M_1$ and $M_2$. Thus, if the device 110 of FIG. 1 uses a single balanced synthetic ferrimagnet in each structure, and if the strength of the external magnetic field can be varied between $-H_{sat}$ and $H_{sat}$, the device 110 will have more than sixteen magnetization orientations.

An exemplary balanced synthetic ferrimagnet 520 may have a rectangular shape and an overall size of 0.5 μm×1.0 μm, and it may include the following stack of materials: 3 nm NiFeCo/0.75 nm Ru/3 nm NiFeCo. Using this exemplary synthetic ferrimagnet in each structure 120 of FIG. 1, the spacing between the structure ends may be 0.5 um. Such structures could trap nanoparticles that are 0.1 to 0.2 um in size.

The synthetic ferrimagnet 520 may instead be unbalanced, whereby the first and second layers 522 and 524 have different coercivities. The coercivities of the first and second ferromagnetic layers 522 and 524 may be made different by using different bit shapes, geometry, composition, thickness, etc.

Figure 6C:
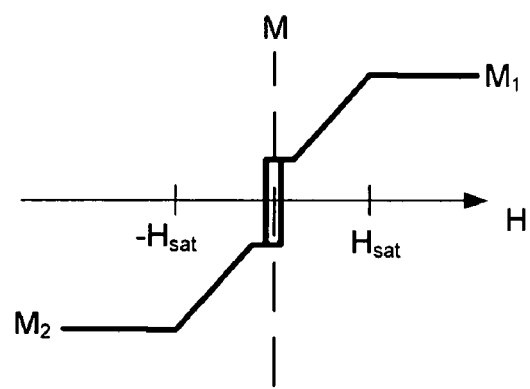

FIG. 6c shows an H-M loop for an unbalanced synthetic ferrimagnet 520. The H-M loop for the unbalanced synthetic ferrimagnet is similar to the H-M loop for the balanced synthetic ferrimagnet, except for hysteresis about H=0.

An exemplary unbalanced synthetic ferrimagnet 520 may have a rectangular shape and an overall size of 0.5 μm×1.0

µm, and it may include the following stack of materials: 5 nm NiFeCo/0.75 nm Ru/2 nm NiFeCo. Using this exemplary synthetic ferrimagnet in each structure 120 of FIG. 1, the spacing between the structure ends may be 0.5 um. Such structures could trap nanoparticles that are 0.1 to 0.2 um in size.

Reference is made to FIG. 5c. The structure shown in FIG. 5c includes an antiferromagnet 530 having first and second ferromagnetic layers 532 and 534 separated by a spacer layer 536. Each ferromagnetic layer 532 and 534 has a magnetization vector oriented along its easy axis. The spacer layer 536 may be made of an electrically conductive, magnetically non-conductive material such as Ru, Re, Rh or Cu. The material and thickness for the spacer layer 536 are selected to promote strong ferromagnetic exchange coupling between the first and second ferromagnetic layers 532 and 534. Thus, the magnetization vector of the first and second layers 532 and 534 always point in the same direction. Net fringe field of the antiferromagnet 530 can be tailored by changing the relative moments of the two ferromagnetic layers 532 and 534. This makes it easier to tailor the fringe fields of an antiferromagnet than a ferromagnet.

Figure 6D:
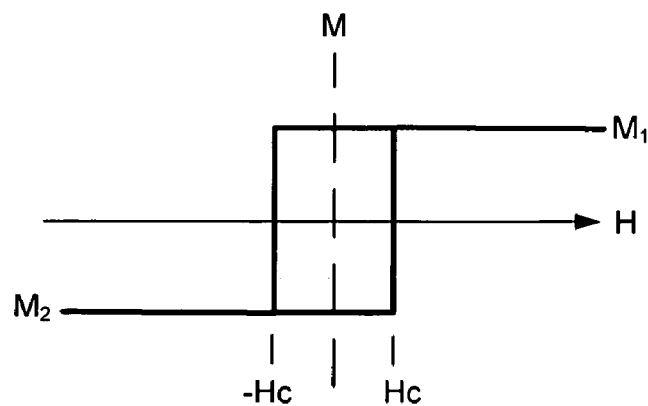

FIG. 6d shows an H-M loop of an anti ferromagnet 530. The H-M loop for the antiferromagnet is similar to the H-M loop of the ferromagnet.

The antiferromagnet 530 is large relative to the nanoparticles. An exemplary antiferromagnet 530 may have a rectangular shape, an overall size of 0.5 µm×1.0 µm, a first layer of 5 nm NiFeCo, a second layer of 2 nm NiFeCo, and a spacer layer of non-magnetic material having a thickness between 5 nm and 50 nm.

Because the structures 120 are relatively large (in comparison to the nanoparticles), its coercivity is low and the external magnetic fields needed to orient the net magnetic moment can be applied by one or more current-carrying conductors near the ferromagnet 510. Direction of the current determines the direction of the magnetization. Although magnetic fields will be created as current flows through the conductors, the magnetic fields will not be large enough to affect the magnetic well.

For the device of FIG. 1, circuitry for supplying currents to the conductors and for controlling the magnetization orientations may be fabricated in the substrate 130. A state machine could be used to switch between different magnetization orientations.

A device according to the present invention is not limited to any particular application. One especially useful application is biosensing.

Figure 7:
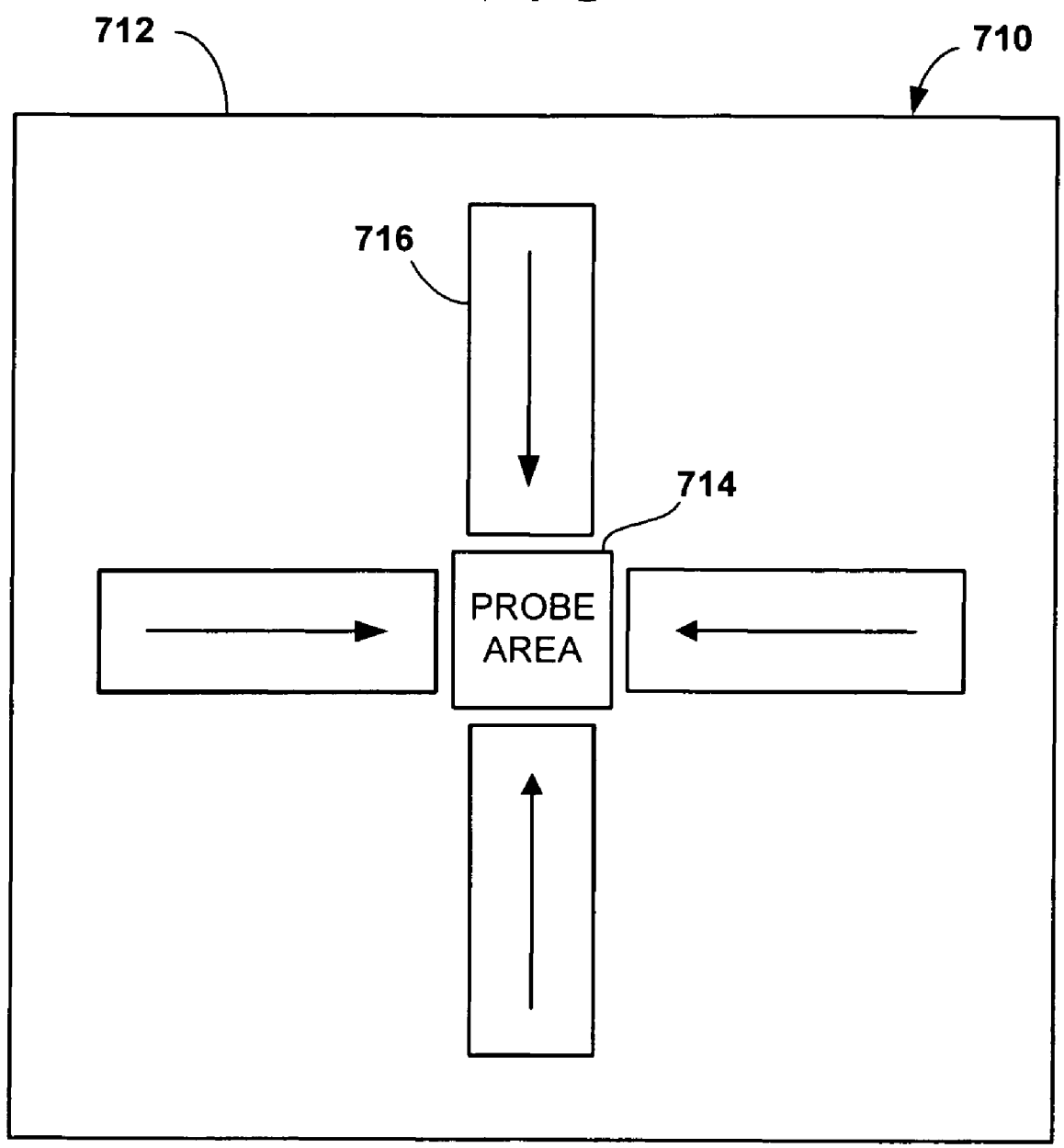
FIG. 7 is an illustration of a biosensor in accordance with an embodiment of the present invention.

Referring now to FIG. 7, a biosensor 710 includes a substrate 712 and a probe area 714 on the substrate 712. The probe area 714 is functionalized to bind selectively to molecules.

The biosensor 710 further includes a plurality of structures 716 having fringe fields that interact to form a magnetic well about the probe area 714. Conductors (not shown) may be formed on the substrate 712 or above the structures 716. The substrate 712 contains circuitry for supplying currents to the conductors. By controlling the direction of the currents through the conductors (and the magnitude of the current in the case of synthetic ferrimagnets), the circuitry can cause the device to switch between different magnetization orientations.

Figure 8:
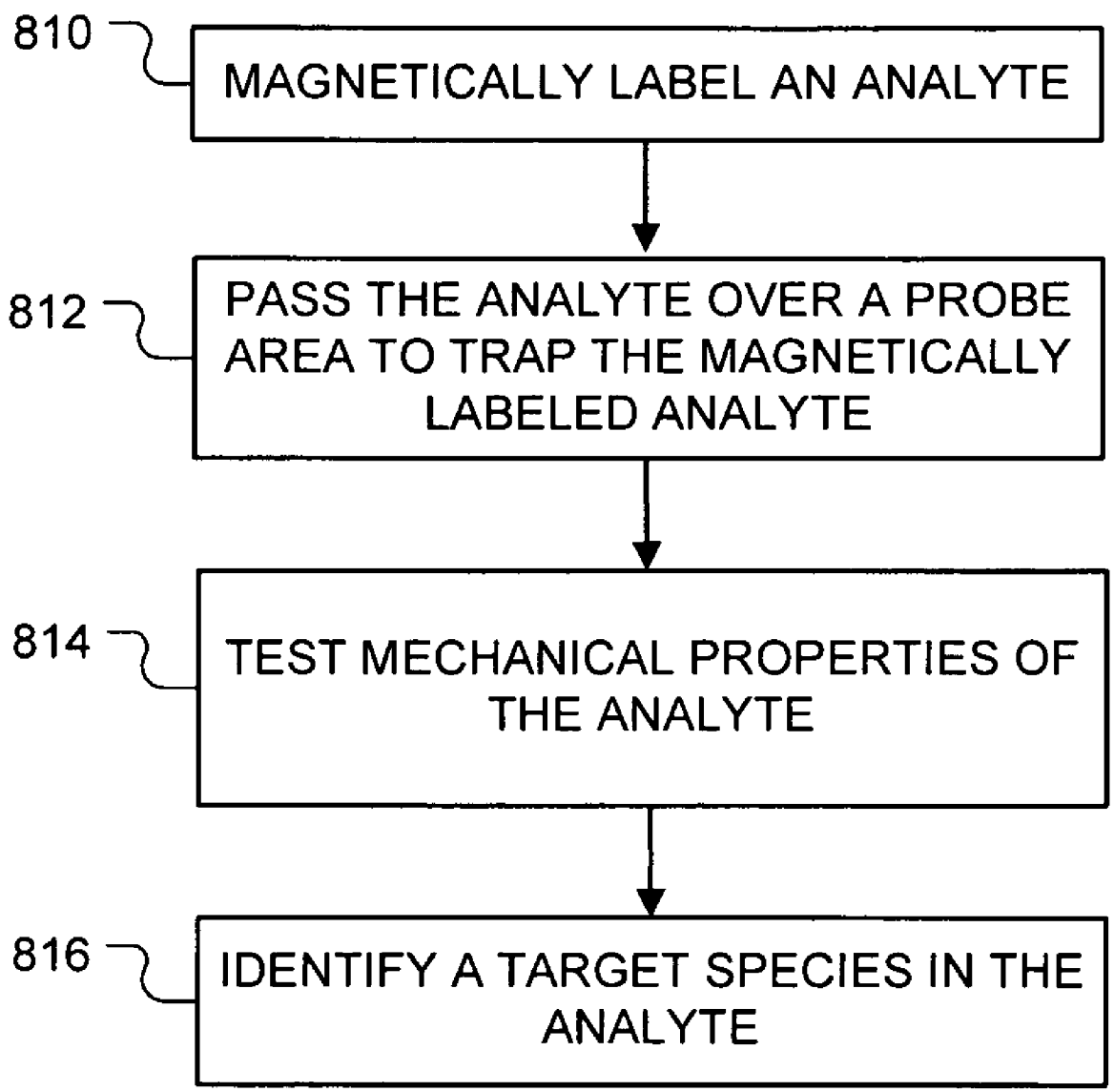
FIG. 8 is an illustration of an exemplary method of using the biosensor of FIG. 7.

Additional reference is now made to FIG. 8, which illustrates a general method of using the biosensor 710. At step 810, an analyte is magnetically labeled. The magnetic labeling may be performed by immobilizing the analyte on ferromagnetic or paramagnetic nanoparticles. The nanoparticles may be coated with a molecule that binds selectively to counterpart molecules in the probe area 714. For example an antigen will bind only to an antibody specific to it. In a typical biosensing reaction, the nanoparticles may be functionalized for a specific reaction, such as a biotin-streptavidin binding chemistry. The analyte may be suspended in a suspension medium (e.g., a fluid).

At step 812, the suspension medium with analyte are passed over the probe area 714. For example, the biosensor 710 may be immersed in the suspension medium. Consequently, nanoparticles within the magnetic well are trapped. Selective binding of the magnetically labeled analyte then occurs with the probe area 714.

At step 814, mechanical properties of the analyte are tested. For example, the magnetic well may be oscillated. As the magnetic well is oscillated, an oscillatory force is applied to the trapped nanoparticles. If a nanoparticle is unbound, the force will cause it to move back and forth in the suspension medium. If a nanoparticle is bound to the probe area, the bonds will be stressed.

The magnetic well can be oscillated to "wiggle" the bonds. Forces on the unbound nanoparticles are measured as the unbound nanoparticles move back in forth in the suspension medium. For example, proteins have conformational changes when their fluid environment is changed (e.g., pH of the solution, the temperature of the fluid). This information can be extracted from the mechanical motion of the nanoparticle. The frequency and amplitude of motion of the nanoparticles will change depending on any binding or other interactions. By observing this motion optically (either directly with a microscope and a digital camera or indirectly by measuring variations in intensity of a beam of light transmitted through or reflected by the sample), the oscillation of the nanoparticles can be measured, and then a frequency shift or an amplitude shift is sensed. The shift provides the basis of the measurement.

The mechanical properties may instead be tested by using the structures 716 to apply a single force of known magnitude in an effort rip apart the bonds. Unbound nanoparticles are then washed away, while a change in the number of nanoparticles is sensed. Measuring the binding force in this way can reveal the strength of the binding force. This, in turn, provides information about the reaction that occurred between the analyte and the probe area 714. Such information could be used to identify the type of reaction.

As an optional step 816, a target species (e.g., a molecule of interest, a protein, a DNA fragment) in the analyte may be identified after its properties have been tested. Testing the properties before performing the identification can be advantageous because a first reference measurement can serve as a calibration for the subsequent sample measurement.

A variety of techniques may be used to identify the target species. As a first example, a magnetoresistive sensor can sense the magnetic moments of the nanoparticles. When passed over the analyte a first time, the magnetoresistive sensor generates a first signal that provides a reference. Unbound magnetic labels are then washed away, and the MR sensor is once again used to detect the presence of magnetic labels that are bound to the probe area. When passed over the analyte a second time, the MR sensor generates a second signal. A comparison of the first and second signals indicates whether the target species was bound to the probe area.

A second example of identifying the target species involves tagging the surface of the nanoparticles with a fluorescent dye and detecting fluorescence. A third example involves measuring the scattered light from the surface of the nanoparticles. A fourth example involves placing two electrodes about the analyte and measuring a change in capacitance between the plates after the nanoparticles (if any) are washed away.

A fifth example involves measuring a change in reluctance between structures 716. This can be done by the change in AC susceptibility of the analyte. If a large number of nanoparticles are washed away, the reluctance will increase. An ac signal can be applied to the analyte by oscillating the magnetic field at a certain amplitude and frequency.

Reference is now made to FIG. 9, which illustrates a biosensing chip 910 including an array 912 of cells 914. Each cell 914 includes a biosensor according to the present invention. Thus, each cell includes a plurality of structures 120 (e.g., ferromagnets, antiferromagnets, or synthetic ferrimagnets) having fringe fields that can interact to form a magnetic well about a probe area.

Only a relatively small number of cells 914 is shown. In practice, arrays of other sizes may be used.

The cells 914 may be "addressed" by selectively applying currents to conductors crossing the cells 914. As shown in FIG. 9, word lines 916 extend along rows of the cells 914, and bit lines 918 extend along columns of the cells 914. Each word line 916 and bit line 918 may include one or more conductors so that the net magnetic moment of each structure can be oriented. In other embodiments, the chip 910 could include only bit lines 918 or only word lines 916.

The chip 910 further includes a steering circuit 920 for steering currents to the word and bit lines 916 and 918 of selected cells 914. The steering circuit 920 may include switches for steering the currents to selected lines 916 and 918. The currents are supplied by a current source 922, which may be on-chip or off-chip. The currents create magnetic fields that cause the device to switch to desired magnetization orientations.

Except for the probe areas, the biosensing chip 910 may be manufactured by using techniques similar to those used in to fabricate MRAM devices.

Although specific embodiments of the present invention have been described and illustrated, the present invention is not limited to the specific forms or arrangements of parts so described and illustrated. Instead, the present invention is construed according to the following claims.

The invention claimed is:

1. A device comprising a plurality of structures, each structure including at least one ferromagnetic layer having fringe fields, wherein the fringe fields of the structures interact to form a magnetic nanoparticle well, said structures being arranged radially around said magnetic nanoparticle well in each of an upper and a lower plane.

2. The device of claim 1, wherein the structures include ferromagnets.

3. The device of claim 1, wherein the structures include antiferromagnets.

4. The device of claim 1, wherein the structures include synthetic ferromagnets.

5. The device of claim 1, wherein said plurality of structures comprises four rectangular structures that are displaced by 90 degrees around said magnetic nanoparticle well.

6. The device of claim 1, wherein each structure has a net magnetic moment that can be aligned between two opposing directions, such that magnetization vectors of the structures can be selectively oriented to oscillate the well.

7. The device of claim 6, further comprising means for causing the magnetic well to oscillate.

8. The device of claim 6, further comprising means for causing the magnetic well to apply a magnetic force to trapped nanoparticles.

9. The device of claim 6, further comprising conductors proximate the structures for selectively orienting the structures.

10. The device of claim 1, wherein the magnetic well is located about an area that is functionalized to bind a specific biomolecule.

11. A biosensor comprising:
a probe area, and
a plurality of structures having fringe fields that interact to form a magnetic well about the probe area, said structures being radially arranged around said magnetic well in each of an upper and a lower plane.

12. The biosensor of claim 11, wherein the structures include ferromagnets.

13. The biosensor of claim 11, wherein the structures include antiferromagnets.

14. The biosensor of claim 11, wherein the structures include synthetic ferromagnets.

15. The biosensor of claim 11, wherein said plurality of structures comprises four rectangular structures that are displaced by 90 degrees around said magnetic well.

16. The biosensor of claim 11, wherein each structure has a net magnetic moment that can be aligned between two opposing directions, whereby magnetization vectors of the structures can be selectively oriented to oscillate the well.

17. The biosensor of claim 16, further comprising circuitry and conductors for causing the magnetic well to oscillate.

18. The biosensor of claim 16, further comprising circuitry and conductors for causing the magnetic well to apply a magnetic force to trapped nanoparticles.

19. The biosensor of claim 16, further comprising conductors proximate the structures for selectively orienting the structures.

20. A method of using the biosensor of claim 11, the method including exposing functionalized nanoparticles to the magnetic well, and causing the magnetic well to oscillate to wiggle bonds between the nanoparticles and the probe area.

21. A method of using the biosensor of claim 11, the method including exposing functionalized nanoparticles to the magnetic well, and causing the magnetic well to apply a single force in an attempt to rip apart bonds between the nanoparticles and the probe area.

22. A biosensor chip comprising:
a substrate;
a plurality of the biosensors of claim 12 on the substrate; and
a plurality of conductors for addressing the biosensors.

23. A method of sensing biomolecules, the method comprising:
forming a magnetic well about a probe area with a plurality of structures arranged radially around said magnetic well in each of an upper and a lower plane, each said structure comprising at least one layer of ferromagnetic material, said magnet well being configured to trap functionalized nanoparticles; and
oscillating the magnetic well to test physical properties of the functionalized nanoparticles.

24. The device of claim 1, further comprising an electromagnet disposed with each structure to selectively reverse a magnetic moment of said ferromagnetic layer of that structure.

25. The device of claim 24, in which each said electromagnet comprises a conductor for carrying electrical current.

26. The device of claim 1, wherein said structures of said upper plane are rotated in position relative to those in said lower plane.

27. The method of claim 23, in which:
said magnetic well is formed by a plurality of structures that have fringe magnetic fields and are arranged such that said fringe magnetic fields form said magnetic well; and
said oscillating is performed by oscillating a magnetic moment of at least one of said structures.

* * * * *

UNITED STATES PATENT AND TRADEMARK OFFICE
CERTIFICATE OF CORRECTION

PATENT NO. : 7,651,871 B2  Page 1 of 1
APPLICATION NO. : 11/290879
DATED : January 26, 2010
INVENTOR(S) : Manish Sharma It is certified that error appears in the above-identified patent and that said Letters Patent is hereby corrected as shown below:

In column 8, line 60, in Claim 24, after "structure" insert -- and configured --.

Signed and Sealed this

Twentieth Day of April, 2010

David J. Kappos
*Director of the United States Patent and Trademark Office*